United States Patent
Wang et al.

(10) Patent No.: US 6,689,353 B1
(45) Date of Patent: Feb. 10, 2004

(54) STABILIZED INTERLEUKIN 2

(75) Inventors: Wei Wang, Alameda, CA (US); Rajiv Nayar, Richmond, CA (US); Michael A. Shearer, Fairfield, CA (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 248 days.

(21) Appl. No.: 09/605,577

(22) Filed: Jun. 28, 2000

(51) Int. Cl.[7] .......................... A61K 38/20; A61K 38/00
(52) U.S. Cl. .......................... 424/85.2; 424/85.1; 514/2; 514/8; 514/12
(58) Field of Search .................. 514/2, 8, 12; 424/85.1, 424/85.2

(56) References Cited

U.S. PATENT DOCUMENTS

| | | | |
|---|---|---|---|
| 4,645,830 A | * 2/1987 | Yasushi et al. | 435/69.52 |
| 5,358,708 A | 10/1994 | Patel | |
| 5,656,730 A | * 8/1997 | Lee | 530/357.3 |
| 5,763,401 A | 6/1998 | Nayar | |
| 6,267,958 B1 | * 7/2001 | Andya et al. | 424/130.1 |

FOREIGN PATENT DOCUMENTS

| | | | | |
|---|---|---|---|---|
| WO | WO-996018 A1 | * 11/1999 | | C12N/15/26 |

OTHER PUBLICATIONS

Taneja et al., Increased thermal stability of proteins in the presence of amino acids, (1994) Biochem Journal, vol:303, 147–153.*
Rishi et al., Role of non-compatible osmolytes in the stabilization of proteins during heat stress, (1998) Biochem Journal, vol:329, 137–143.*
Pikal, M. J., Freeze–Drying of Proteins, PartII: Formulation Selection (1990), Biopharm, Vol 3, No. 9, pp 26–30.*
Chang, B. S. et al, Development of an Efficient Single Step Freeze–Drying Cycle for Protein Formulations, Pharm. Res., Vol 12, No. 6 pp 831–837 (1995), Plenum Publ. Corp.
Wang, W., Lyophilization and Development of Solid Protein Pharmaceuticals, International Journal of Pharmaceutics, 203:1–60, 2000.

* cited by examiner

*Primary Examiner*—Gary Kunz
*Assistant Examiner*—Jegatheesan Seharaseyon
(74) *Attorney, Agent, or Firm*—John W. Mahoney

(57) ABSTRACT

A stable pharmaceutical preparation comprising Human interleukin-2 or a variant thereof and a stabilizing amount of histidine. A preferred formulation includes glycine and sucrose and a variant of IL-2 having a single mutation, N88R. The preferred formulation is in lyophilized form which, on reconstitution with an aqueous diluent, results in a solution having a pH ranging from about 5.0 to 6.5.

6 Claims, 2 Drawing Sheets

SEQUENCE LISTING

```
<160> NUMBER OF SEQ ID NOS: 8

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Leu Lys
    50                  55                  60
```

```
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 2
<211> LENGTH: 465
<212> TYPE: DNA
<213> ORGANISM: Homo sapiens

<400> SEQUENCE: 2
atgtacagga tgcaactcct gtcttgcatt gcactaagtc ttgcacttgt cacaaacagt      60
gcacctactt caagttctac aaagaaaaca cagctacaac tggagcattt actgctggat    120
ttacagatga ttttgaatgg aattaataat tacaagaatc ccaaactcac caggatgctc    180
acatttaagt tttacatgcc caagaaggcc acagaactga acatcttca gtgtctagaa      240 gaagaactca aacctctgga ggaagtgcta aatttagctc aaagcaaaaa ctttcactta    300
agacccaggg acttaatcag caatatcaac gtaatagttc tggaactaaa gggatctgaa    360
acaacattca tgtgtgaata tgctgatgag acagcaacca ttgtagaatt tctgaacaga    420
tggattacct tttgtcaaag catcatctca acactgactt gataa                    465

<210> SEQ ID NO 3
<211> LENGTH: 30
<212> TYPE: DNA
<213> ORGANISM: Homo sapiens

<400> SEQUENCE: 3
cctcaactcc tgaattcatg tacaggatgc                                       30

<210> SEQ ID NO 4
<211> LENGTH: 31
<212> TYPE: DNA
<213> ORGANISM: Homo sapiens

<400> SEQUENCE: 4
ggaagcggat ccttatcaag tcagtgttga g                                     31

<210> SEQ ID NO 5
<211> LENGTH: 36
<212> TYPE: DNA
<213> ORGANISM: Homo sapiens

<400> SEQUENCE: 5
gcacttgtca caaacaccat ggcacctact tcaagt                                36

<210> SEQ ID NO 6
<211> LENGTH: 28
<212> TYPE: DNA
<213> ORGANISM: Homo sapiens
<220> FEATURE:
<221> NAME/KEY: misc_feature
<222> LOCATION: 17, 18, 19
<223> OTHER INFORMATION: n = A,T,C or G
```

-continued

```
<400> SEQUENCE: 6
ggagcattta ctgctgnnnt tacagatg                                        28

<210> SEQ ID NO 7
<211> LENGTH: 30
<212> TYPE: DNA
<213> ORGANISM: Homo sapiens
<220> FEATURE:
<221> NAME/KEY: misc_feature
<222> LOCATION: 15, 16, 17
<223> OTHER INFORMATION: n = A,T,C or G

<400> SEQUENCE: 7
gggacttaat cagcnnnatc aacgtaatag                                      30

<210> SEQ ID NO 8
<211> LENGTH: 28
<212> TYPE: DNA
<213> ORGANISM: Homo sapiens
<220> FEATURE:
<221> NAME/KEY: misc_feature
<222> LOCATION: 15, 16, 17
<223> OTHER INFORMATION: n = A,T,C or G

<400> SEQUENCE: 8
ggattacctt ttgtnnnagc atcatctc                                        28
```

STABILIZED INTERLEUKIN 2

BACKGROUND OF THE INVENTION

FIELD

The invention is generally related to the field of pharmaceutical formulations. More specifically, the invention is directed to a stabilized, therapeutically active Interleukin-2 formulation capable of selectively activating T cells (PHA-blasts) and, very preferably, including an IL-2 mutein demonstrating reduced activation of Natural Killer ("NK") cells. The stabilized compositions having the preferred properties include variants of IL-2 described below.

BACKGROUND

As discussed in a related application PCT/US 99/10643 published Nov. 25, 1999, Interleukin 2 (IL-2) is a potent immune stimulator, activating diverse cells of the immune system, including T cells, B cells, and monocytes. IL-2 is also a potent and critical growth factor of T cells. It was by virtue of these activities that IL-2 was tested for its ability to treat cancer. Human IL-2 is a FDA approved drug for the treatment of metastatic renal carcinoma and metastatic melanoma. The use of IL-2 in eligible patients is restricted due to the severe toxicity associated with IL-2 therapy; it is estimated that at best only 20% of eligible patients actually receive therapy. The toxicities associated with IL-2 therapy include severe fever, nausea, vomiting, vascular leak and serious hypotension. Despite these toxicities, however, IL-2 is effective for its approved indications. Variants of IL-2 having reduced toxicity are the subject matter of application WO 99/60128.

Significant information on stabilization of IL-2 and other therapeutic protein formulations is available. The currently approved Human IL-2 preparation (Proleukin® IL-2, Chiron Corporation) is a freeze-dried preparation which includes mannitol, sodium dodecyl sulfate (SDS) and a phosphate buffer. Other formulated therapeutic proteins, including IL-2, are described in the following references. Fernandes et al., 1986, Pharmaceutical compositions of microbially produced interleukin-2 (U.S. Pat. No. 4,604,377) describes a freeze-dried formulation containing a stabilizer (mannitol) and a solubilizing agent such as sodium dodecyl sulfate or sodium deoxycholate sulfate at about 100 to about 250 ug per mg of IL-2. The formulation for the currently available Proleukin® IL-2 product is believed to be described in this reference.

Patel, 1994 Stabilization of protein formulations (U.S. Pat. No. 5,358,708) describes aqueous formulations of an interferon, a granulocyte-macrophage colony-stimulating factor or an interleukin having extended storage lifetimes by incorporating methionine, histidine or mixtures thereof. Although reference is made to several interleukins, including IL-2, in work done with an IL-4 formulation the patentees found histidine to be less effective as a stabilizer than methionine, under conditions of the stabilizer test used.

Shaked, et al., 1991, Pharmaceutical compositions of recombinant interleuken-2 and formulation processes (U.S. Pat. No. 5,037,644) describes formulations which are either in freeze-dried or liquid form. The excipients of the formulation include a non-ionic polymeric detergent such as Triton X405, Triton X305, PEG (4000) monostearate, Tween 80 and Tween 20 at concentrations of about 0.001% to about 5%, a bulking/stabilizing agent such as sucrose, fructose, dextrose, maltose, glucose, dextran, mannitol, sorbitol, inositol, galactitol, xylitol, lactose, trehalose, human serum albumin and bovine serum albumin, and a buffering agent such as glycine, citrate, or phosphate in a concentration range from about 10 mM to about 50 mM with a pH ranging from about 3 to about 7. The concentration (wt/vol) of the polyol sugar bulking agent ranges from about 0.025% to about 10%.

Roskam et al., 1995, Drugs containing a glycosylated interleukin-2 (U.S. Pat. No. 5,417,970) describes a freeze-dried formulation containing hydrolyzed gelatin (or human serum albumin) and alanine with a pH 6.5.

Hora et al., 1992, Pharmaceutical composition for interleukin-2 containing physiologically compatible stabilizers (U.S. Pat. No. 5,078,997) describes formulations which are either liquid or freeze-dried. Formulations may contain one or a combination of stabilizers such as arginine, carnitine, betaine, pyridoxine polyvinylpyrrolidone, salts of capric acid, sugars, sugar alcohols, serum albumin, and citrate at pH 5.0–8.5 buffer. The concentration of stabilizers is between 0.2 and 3.0% (w/v) for arginine, between 0.2 and 3.0% (w/v) for carnitine, between 2 and 6% (w/v) for sucrose, and 0.01 and 0.3M for citrate.

Yasushi et al., 1987 Stable composition of interleukin-2 and albumin (U.S. Pat. No. 4,645,830) describes a stable aqueous formulation that contains human serum albumin (0.1–50 mg/ml) with or without a reducing excipient such as glutathione, thioctic acid, N-acetylcysteine, or ascorbic acid (concentration of 0.05–20 mg/ml) at pH between 3 to 5.5. The albumin formulation may contain a monoamino aliphatic amino acid, a cyclic amino acid, a monosaccharide, a sugar alcohol or monoamino aliphatic amino acid (concentration of 5 to 50 mg/ml).

Lee et al., 1989 Pharmaceutical plasma protein formulations in low ionic strength media; sodium chloride and/or potassium chloride, lysine hydrochloride, and histidine (U.S. Pat. No. 4,877,608) describes stable factor VIII and other plasma protein formulations in low ionic strength media which comprises: sodium chloride, potassium chloride or mixtures thereof; lysine hydrochloride; and histidine as the buffering agent.

Nayar, 1998 stabilized albumin-free recombinant Factor VIII preparation having a low sugar content (U.S. Pat. No. 5,763,401 and U.S. Pat. No. 5,874,408) describes an albumin free stabilized FVIII formulation including glycine, histidine, sucrose and NaCl.

In attempting to find a stable IL-2 formulation (especially for the preferred IL-2 mutein (N88R) of WO 99/60128), we have now found a very stable and pharmaceutically acceptable formulation for biologically active and useful Human IL-2. Our discovery is based on addressing what we believe is the basic mechanism responsible for stability, as described below.

SUMMARY OF INVENTION

The present invention is a pharmaceutical composition or formulation of IL-2 or variants (muteins) thereof stabilized with histidine. Preferably, the composition comprises a mixture resulting in a solution of low ionic strength (e.g.

<0.1) and includes other stabilizers such as sugars and amino acids, preferably sucrose and glycine. The formulation may include from 0 to 0.9 wt. % NaCl. The composition is albumin-free and the formulation in lyophilized form can be rapidly reconstituted (<1 minute) with water. The composition solubilizes under physiologically acceptable pH conditions, preferably at a pH ranging from about 5.0 to about 6.5, without the use of surfactants such as sodium dodecyl sulfate. The reconstituted solution is near isotonicity and can be administered both subcutaneously and intravenously. In a very preferred embodiment, the IL-2 of the composition is a mutein having a single amino acid substitution, preferably the N88R variant described in WO 99/60128.

The very preferred composition has a protein concentration of 1–5 mg/ml and comprises the following in aqueous form (on a wt/wt basis):

| | |
|---|---|
| IL-2 | 0.1–0.5 wt % |
| Histidine | 0.08–1.6 wt % |
| NaCl | 0–0.9 wt % |
| Sucrose | 1–10 wt % |
| Glycine | 0–3 wt %, at a |
| pH of | 5 to 6.5. |

Details of our formulation and how it was discovered are described below.

SPECIFIC EMBODIMENTS

As used herein, the term IL-2 includes both active wild type IL-2 and its biologically active variants or muteins such as those described in WO 99/60128. In the examples below we used an IL-2 known as IL-2(N88R) which is a recombinant mutein of human IL-2, with asparagine (N) at amino acid position 88 mutated to arginine (R). This mutein was expressed from Chinese hamster ovary (CHO) cells and comprised a mixture of both glycosylated and non-glycosylated forms. It is described in WO 99/60128 cited above as a related application.

The objective that led to this invention was the need to identify a lyophilized dosage form for the preferred IL-2 mutein that was albumin-free with acceptable stability. Since, the bioassay for IL-2 was an insensitive measure of stability, we used quantitation of soluble IL-2 by reverse phase HPLC as the stability indicating assay. As used herein, the terms "stable" or "stabilized" mean reduction of soluble IL-2 quantity by reverse-phase HPLC to no less than 90% of original soluble quantity after storage for four months at 40° C. (see tables 3 and 4 below). Additional stability-indicating assays employed included Aggregation Index, a measure of aggregation by UV/VIS spectrophotometry and determination of soluble aggregates by size-exclusion HPLC. In addition to a stable product, rapid reconstitution (less than 1 minute) of the lyophilisate is highly preferred. Finally, the formulation in a lyophilized dosage form with acceptable stability which could be easily lyophilized in production freeze dryers was desired.

Figure 1:
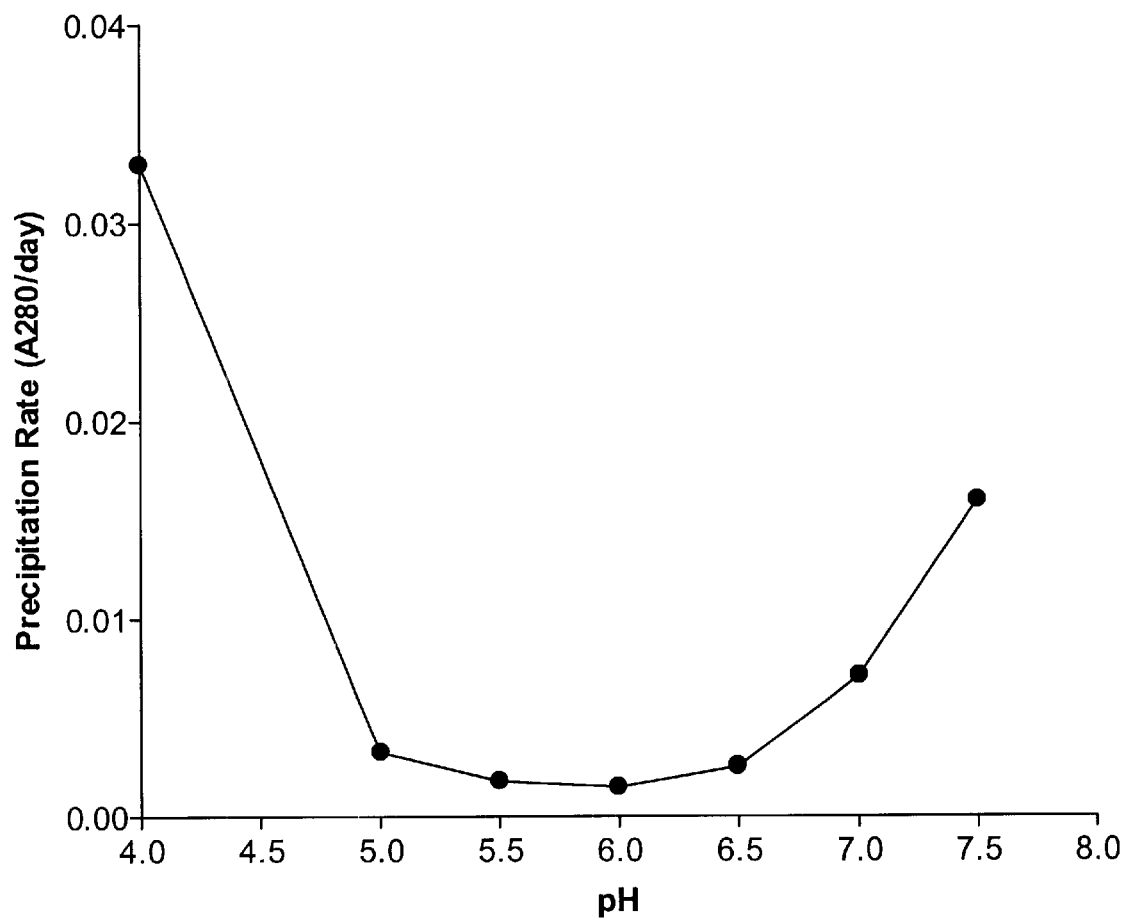
FIG. 1 is a graph illustrating the optimum pH range for an aqueous IL-2 solution.
Figure 2:
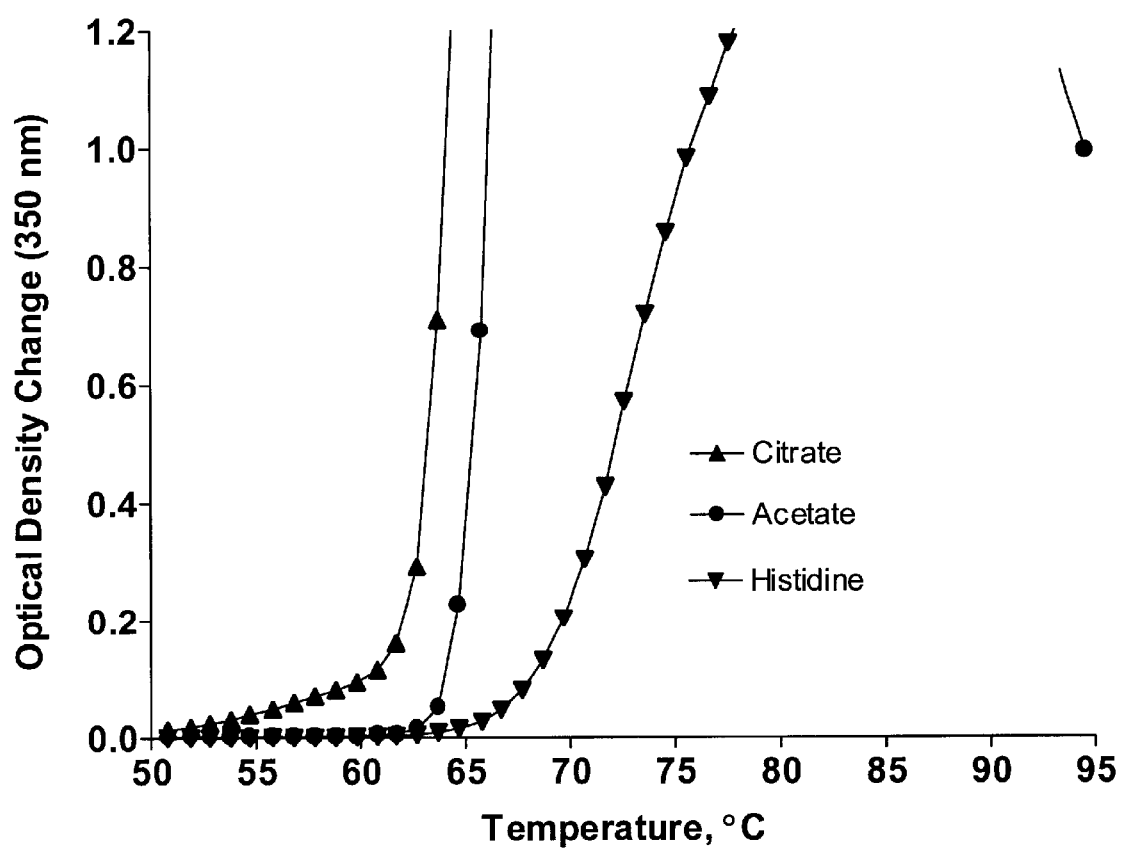
FIG. 2 compares the stabilizing effect of histidine to acetate and citrate on IL-2 aggregation induced by heating the protein solution at 1 C°/min from 25° C. to 95° C.

Aqueous. stability studies carried out during preformulation investigations indicated that IL-2(N88R) readily aggregates in the liquid state and the aggregation was pH-dependent. Two preformulation stability studies were conducted: a pH profile of IL-2(N88R) and stability in the presence of different buffer excipients. The objectives of these studies were to identify a suitable pH range for IL-2(N88R) and a suitable buffering excipient for aqueous stability (reduced aggregation potential). In generating the pH profile, IL-2 solutions were prepared with different pH conditions and stored under accelerated temperature conditions (40° C.). Samples were analyzed at different time intervals and rates of aggregation calculated. As shown in FIG. 1, the optimal pH range for low aggregation rates was identified between pH 5.0 and 6.5. Histidine, acetate, and citrate were identified as pharmaceutical buffering agents for IL-2(N88R) in this pH range and were evaluated at a concentration of 20 mM in IL-2 (N88R) solutions containing 1 mg/ml IL-2 (N88R) and 150 mM (0.9 wt %) NaCl. These samples were heated from 25° C. to 95° C. at 1° C. per minute and precipitation was monitored by UV spectrophotometry at 350 nm. As shown in FIG. 2, to our surprise, histidine significantly stabilized IL-2(N88R) over the other buffer excipients at pH 5.5 as indicated by an increase in the onset temperature of precipitation. The onset temperatures in the presence of citrate, acetate, and histidine were 62° C., 64° C., and 70° C., respectively. Studies such as these demonstrated that histidine could be used not only as a buffering agent but also a stabilizer for IL-2 under aqueous conditions.

For development of a lyophilized dosage form, other excipients that are used by those familiar with the art were investigated. These included bulking agents and cryoprotectants such as glycine, sucrose, and mannitol. Two surfactants were also evaluated as stabilizers for IL-2(N88R), since aggregation was one of the instability mechanisms for the molecule during the aqueous stability studies. The results of these studies are summarized in the examples below. They show that to our surprise histidine has selective stabilizing effects on IL-2 over other excipients, such as citrate for example.

EXAMPLE 1

The stability of liquid IL-2(N88R) at different pHs was examined at 40° C. The results showed that IL-2(N88R) precipitation rate was lowest between pH 5.0 to 6.5 (FIG. 1). Therefore, pH 5.5 was chosen as the optimal formulation pH in liquid state and for preparation of lyophilized formulations.

EXAMPLE 2

We examined the potential effect of different buffering agents on the stability of IL-2(N88R). The buffering agents we examined included citrate, acetate, and histidine. These buffering agents were used at 20 mM in IL-2(N88R) solutions containing 1 mg/ml IL-2(N88R) and 150 mM (0.9 wt %) NaCl. These stability samples were heated from 25° C. to 95° C. at 1° C. per minute while being monitored by UV/VIS spectrophotometry. Histidine significantly stabilized IL-2(N88R) by increasing the precipitation temperature and by decreasing the precipitation rate in comparison with acetate and citrate (FIG. 2). Table 1 shows the onset precipitation temperatures of IL-2(N88R) in the presence of these three buffering agents. The onset precipitation temperature was arbitrarily defined as the temperature at which the optical density at 350 nm ($OD_{350}$) reaches a certain level (0.2 and 1.0 in the case of $OD_{350}$). The precipitation temperature of IL-2(N88R) in the presence of histidine was several degrees higher than those in the presence of the other two buffering agents. This example demonstrated that histidine may be a specific stabilizer in addition to being used as a buffering agent for IL-2(N88R) in the liquid state.

TABLE 1

Precipitation Temperature (OD$_{350}$ = 0.2 and OD$_{350}$ = 1.0) of IL-2(N88R) in Different Buffers

| Buffering Agents | Precipitation Temperature, °C. (when OD$_{350}$ = 0.2) | Precipitation Temperature, °C. (when OD$_{350}$ = 1.0) |
|---|---|---|
| Citrate | 62° C. | 64° C. |
| Acetate | 64° C. | 66° C. |
| Histidine | 70° C. | 76° C. |

EXAMPLE 3

In an effort to evaluate further the stabilizing effect of histidine, lyophilized IL-2(N88R) was prepared from different aqueous formulations (see Table 2). Most of the formulations contained 2 wt % glycine as a bulking agent and 1 wt % sucrose as a stabilizer. Mannitol at 5 wt % was used in a formulation as a comparator to Proleukine®, a commercialized product of IL-2. Two surfactants, Tween 80 and Pluronic F68 both at 0.1 wt %, were evaluated for prevention of protein surface adsorption and aggregation. All the formulations contained either histidine or citrate as a buffering agent with a pH adjusted to 5.5. Citrate was included to distinguish the stabilizing effect of histidine from that of citrate at pH 5.5. These lyophilized formulations were stored at 40° C. and were analyzed by a number of analytical methods that included UV/VIS spectrophotometry, SEC-HPLC, and RP-HPLC.

Table 3 shows the stability of IL-2(N88R) in a number of formulations as assessed by UV/VIS spectrophotometry for aggregation, amount of soluble aggregates by size-exclusion HPLC (SEC-HPLC), and percent recovery of the protein by reverse-phase HPLC (RP-HPLC). Samples were analyzed after lyophilization and stored at an accelerated storage temperature of 40° C. for four months. The lyophilization process did not change the net aggregation index of IL-2 (N88R) from the pre-lyophilization state, suggesting that IL-2(N88R) tolerated the lyophilization process with respect to protein aggregation/precipitation. After storage at 40° C. for four months, a significant increase in net aggregation index was observed for the formulation containing citrate (B), Pluronic F-68 (D) or mannitol (E). These results indicated that inclusion of either citrate or mannitol, Tween-80 or Pluronic F-68 did not offer any protection of IL-2(N88R) aggregation in the solid state during storage. Formulations A and F did not show a significant change in the aggregation index, suggesting that inclusion of histidine, glycine, and sucrose with 1 or 5 mg/ml IL-2(N88R) resulted in a stable product.

However, significant amounts of soluble aggregates were found in the formulation containing Tween-80 even before lyophilization (Table 3), indicating that Tween-80 promotes formation of soluble IL-2(N88R) aggregates, although formation of insoluble aggregates may be inhibited. Since Pluronic F-68 (formulation D) also caused significant formation of soluble aggregates, surfactants may not be compatible with IL-2(N88R). Only the formulations that contained 2% glycine, 1% sucrose, and 20 mM (0.31 wt %) histidine (A, F) did not show any detectable formation of soluble aggregates after storage of the lyophilized formulation at 40° C. for four months, suggesting again that IL-2 (N88R) was stabilized by histidine.

The total recovery of soluble IL-2(N88R) after lyophilization and storage was determined by RP-HPLC (Table 3). The recovery of IL-2(N88R) after lyophilization was greater than about 96% for all formulations except for the formulation containing mannitol. After storage of these formulations at 40° C. for 4 months, approximately 92% of IL-2 (N88R) was recovered in formulations A and F containing 2% glycine, 1% sucrose and 20 mM (0.31 wt %) histidine containing 1 and 5 mg/ml IL-2(N88R). These data (greater than 90% recovery of IL-2 (N88R) for formulations A and F) again suggest that histidine stabilizes IL-2(N88R) while surfactants destabilize the protein.

TABLE 2

Composition of Lyophilized IL-2(N88R) Formulation

| | Formulation ID | | | | | |
|---|---|---|---|---|---|---|
| | A | B | C | D | E | F |
| IL-2(N88R), mg/mL | 1 | 1 | 1 | 1 | 1 | 5 |
| Glycine, wt % (w/w) | 2 | 2 | 2 | 2 | 0 | 2 |
| Sucrose, wt % (w/w) | 1 | 1 | 1 | 1 | 0 | 1 |
| Mannitol, wt % (w/w) | 0 | 0 | 0 | 0 | 5 | 0 |
| Sodium Citrate, wt % (w/w) | 0 | 0.6 | 0 | 0 | 0 | 0 |
| Histidine, wt % (w/w) | 0.31 | 0 | 0.31 | 0.31 | 0.31 | 0.31 |
| Tween 80, wt % (v/w) | 0 | 0 | 0.1 | 0 | 0 | 0 |
| Pluronic F68, wt % (w/w) | 0 | 0 | 0 | 0.1 | 0 | 0 |
| pH | 5.5 | 5.5 | 5.5 | 5.5 | 5.5 | 5.5 |

TABLE 3

Stability of IL-2(N88R) during Lyophilization and Storage of the Lyophilized Formulation at 40° C. for 4 months.

| | Formulation ID | | | | | |
|---|---|---|---|---|---|---|
| | A | B | C | D | E | F |
| Aggregation Index (%) | | | | | | |
| Before lyophilization | 4.4 | 5.2 | 1.5 | 4.7 | 5.6 | 1.6 |
| After lyophilization | 5.2 | 5.1 | 0.7 | 1.5 | 3.8 | 1.6 |
| 4 months at 40° C. | 2.9 | 13.9 | 2.4 | 14.3 | 20.8 | 3.3 |
| Soluble Aggregates (%) by SEC-HPLC | | | | | | |
| Before lyophilization | ND[a] | ND | 4.4% | ND | ND | NA[b] |
| After lyophilization | ND | ND | 7.2% | ND | ND | NA |
| 4 months at 40° C. | ND | 4.2% | 32.9% | 15.9% | 12.2% | NA |
| Recovery (%) by RP-HPLC | | | | | | |
| Before lyophilization | 100 | 100 | 100 | 100 | 100 | 100 |
| After lyophilization | 96.5 | 95.7 | 96.4 | 99.4 | 91.7 | 97.8 |
| 4 months at 40° C. | 92.5 | 82.9 | 71.9 | 84.3 | 79.1 | 91.7 |

[a]ND = not detectable
[b]NA = not available

EXAMPLE 4

Wild-type IL-2 was also lyophilized from an aqueous formulation of the same composition as formulation A. The stability data for the wild-type IL-2 at 40° C. was comparable to those for IL-2(N88R) (Table 4).

TABLE 4

Stability of Wild-type IL-2(N88R) Formulation during Lyophilization and Storage of the Lyophilized Formulation

| Conditions | Aggregation Index (%) | Soluble Aggregates (%) | Recovery (%) |
|---|---|---|---|
| Before lyophilization | 4.2 | ND[a] | 100 |
| After lyophilization | 5.1 | ND | 93.6 |
| 4 months at 40° C. | 4.3 | ND | 93.0 |

[a]ND = not detectable

DISCUSSION

Human IL-2 has 133 amino acids that form six helical structures (A–F). Four of these helixes form what is termed a tetra-helix bundle motif. The intramolecular disulfide bond between $cys^{58}$ and $cys^{105}$ is located on the extended loops between the helices. The free $cys^{125}$ is located on helix F that incorporates amino acids 117–133.

The surprise finding that histidine is a specific stabilizer of IL-2 suggests that histidine may interact with IL-2 in a specific manner which results in stabilizing the molecule in both the aqueous and lyophilized states. One of the major mechanisms of instability of IL-2 is aggregation that results from the formation of oligomers due to thiol-disulfide exchange reactions. Hence, one can hypothesize that histidine may in fact inhibit or reduce the thiol-disulfide exchange reactions in IL-2. Since wild type IL-2, IL-2 (N88R) and possibly other IL-2 variant molecules that have one disulfide bond and a free cysteine ($Cys^{125}$), the free —SH group on $Cys^{125}$ could easily react with the disulfide bond via the thiol/disulfide exchange pathway thereby resulting in aggregation/precipitation events.

The mechanism of thiol/disulfide exchange has been described recently by Bulaj et al. (Ionization-reactivity relationships for cysteine thiols in polypeptides. Biochemistry 1998 June 23;37(25):8965–72). In studies of model peptides and proteins, the reaction rate has been shown to be sensitive to electrostatic forces as well as to the secondary structure of the proteins. The electron distribution around a sulfur atom in a thiol can be influenced by the presence of nearby charges and through-bond inductive effects which can alter the $pK_a$ of the thiol. For example, increased reactivity of the thiols in the thiol/disulfide exchange can be attributed to the lowering of its $pK_a$ due to the presence of either nearby positive charges or peptide dipole contributions from a nearby alpha-helical structure. In contrast, negative charges near the thiol group can raise the $pK_a$ of the thiol and lead to lower thiol/disulfide reaction rates. This proposed mechanism is also supported by other studies, where stabilization of the highly reactive thiolate ions by neighboring positively-charged residues has been demonstrated for protein tyrosine phosphatase (Zhang and Dixon, 1993 Active site labeling of the Yersinia protein tyrosine phosphatase: the determination of the pKa of the active site cysteine and the function of the conserved histidine 402. Biochemistry 1993 September 14;32(36):9340–5) and protein disulfide isomerase (Kortemme et al., Electrostatic interactions in the active site of the N-terminal thioredoxin-like domain of protein disulfide isomerase. Biochemistry 1996 November 19;35(46):14503–11).

Based the these properties of the thiol/disulfide exchange reaction, one can envision a stabilization mechanism where histidine plays either a kinetic or a thermodynamic role in the stabilization of IL-2(N88R). There are five glutamic acid residues (57, 60, 61, 62, and 106) near the disulfide bridge $Cys^{58}$–$Cys^{105}$. Specific binding of histidine to these negatively-charged residues could lead to a kinetic barrier for the thiol/disulfide exchange reaction or the binding of histidine near the disulfide bridge could thermodynamically stabilize the IL-2 molecule into a conformation that is less prone to aggregation reactions. In addition, the His-Glu ionic interactions may also create steric hindrance that would further reduce the rate-determining step in the thiol/disulfide exchange which is the formation of an intermediate transition state between the three participating sulfur atoms. The accessibility of histidine to the glutamic acid residues is very likely because the disulfide bond is located on an extended loop on the protein surface.

Given the above examples it is expected that variations of the inventions disclosed herein will occur to those skilled in the art. Accordingly, it is intended that the above examples should be construed as illustrative only and that the inventions disclosed herein should be limited only by the following claims.

We claim:

1. A stable lyophilized pharmaceutical composition comprising approximately 1 to 4 milligrams per milliliter of a human IL-2 mutein and a stabilizing mixture comprising histidine, glycine, and sucrose, wherein said human IL-2 mutein consists of the amino acid sequence of wild-type human IL-2 with one substitution consisting of the replacement of the amino acid asparagine at position 88 in the wild-type human IL-2 with the amino acid arginine.

2. The stable lyophilized composition of claim 1, wherein the histidine is present at approximately 0.06–1.8% measured by weight.

3. The stable lyophilized composition of claim 1, wherein the glycine is present at approximately 1–3% measured by weight.

4. The stable lyophilized composition of claim 1, wherein the sucrose is present at approximately 0.5–3% measured by weight.

5. The stable lyophilized composition of claim 1 in aqueous form having a pH ranging from about 5.0 to 6.5.

6. A stable lyophilized pharmaceutical composition, which upon aqueous reconstitution comprises the following:

1.0–4.0 mg/ml of a human IL-2 mutein consisting of the amino acid sequence of wild-type human IL-2 with one substitution consisting of the replacement of the amino acid asparagine at position 88 in the wild-type human IL-2 with the amino acid arginine,

| | |
|---|---|
| Histidine | 0.08–1.6% wt, |
| NaCl | 0–0.9 wt % |
| Sucrose | 1–10% wt, and |
| Glycine | 0–3% wt at a |
| pH of | 5–6.5. |

* * * * *